Figure 1:
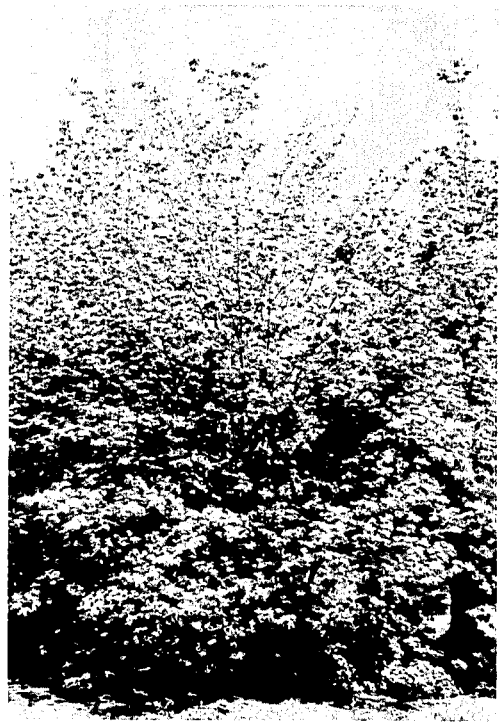

United States Patent [19]

Orton, Jr.

[11] Patent Number: Plant 7,207

[45] Date of Patent: Mar. 27, 1990

[54] DOGWOOD TREE—'STELLAR PINK'

[75] Inventor: Elwin R. Orton, Jr., Somerville, N.J.

[73] Assignee: Rutgers University, New Brunswick, N.J.

[21] Appl. No.: 262,685

[22] Filed: Oct. 26, 1988

[51] Int. Cl.[4] ..... A01H 5/00

[52] U.S. Cl. ..... Plt./51

[58] Field of Search ..... Plt./51

*Primary Examiner*—James R. Feyrer

*Attorney, Agent, or Firm*—Frank B. Robb

[57] ABSTRACT

An interspecific hybrid of *Cornus kousa* and *Cornus florida,* which is a large bracted, vigorous, highly floriferous, flowering tree, most nearly like its parent *C. kousa,* which plant is upright rather than low and spreading as in *C. florida,* the instant plant being more fully branched and spreading as compared with *C. kousa,* with a period of floral display that is intermediate to *C. kousa* and *C. florida,* exhibiting attractive pink bracts unlike those of any other hybrid of *C. kousa*×*C. florida.*

2 Drawing Sheets

BACKGROUND OF THE INVENTION

This invention relates to dogwood trees and particularly to the selection of a superior $F_1$ hybrid, after the interspecific hybridization of an unnamed plant of *Cornus kousa* (K2)×a plant of *Cornus florida* 'Sweetwater' (D20).

The selection was part of a long continuing program of development of new plants of dogwood, and as far as is I am aware there has been no hybrid from the combination of *C. kousa* and *C. florida* known in the plant art.

Plants of this hybrid are vigorous and upright in habit, and floriferous. The broad, rounded, overlapping bracts are light pink and provide a floral display from about May 18 to June 2. In field trials where the plant was developed, the plants have been free of infestation by the dogwood borer and have not exhibited "dogwood decline".

The plant is susceptible of being grown wherever plants of *C. kousa* and *C. florida* are grown although they have not been tested in any widespread areas by me or under my direction.

In this program of hybridization which I have carried on for a number of years, there have been developed a substantial number of what I feel are commercially desirable dogwood trees, particularly because they exhibit their attractive bracts at times when the other known dogwoods such as *C. kousa* and *C. florida* are not so exhibiting.

In this program I have developed a number of white dogwoods as well as this particular dogwood which I have determined should be denominated as 'Rutgan', and is distinguished from the others which were developed and which are not presently patented by the fact that it is a pink-bracted dogwood.

The hybrid of my invention, has been asexually reproduced by stem cuttings so as to determine that it does in fact come true in successive generations and the pink coloration is of desirable attractiveness for commercial display in my opinion.

In the following detailed description which includes some comments in respect to various aspects of the plant, there is provided in addition, a drawing which discloses the tree in color and the colors are referred to the Royal Horticulture Colour Chart for individual notations and comments made are accurate to describe the plant.

FIG. 1 discloses a tree of my new cultivar in full bloom.

Figure 2:
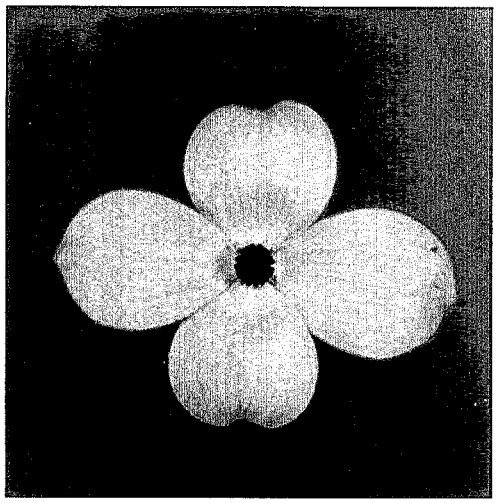

FIG. 2 discloses four floral bracts with central subtended flower heads, typical of my new cultivar.

The coloration is shown in the drawing made from a photograph which thus reproduces the same as near as is possible to the colors of the actual plant with the notations referred thereto.

Parentage:

*Seedling.*—$F_1$ interspecific hybrid.

*Seed parent.*—Unnamed seedling of *Cornus kousa* Hance.

*Pollen parent.*—*Cornus florida* L. cv. 'Sweetwater'.

Propagation:

*Method of asexual propagation.*—Holds its distinguishing characteristics through asexual propagation by such means as grafting, budding, or rooting of softwood or semi-hardwood stem cuttings.

*Classification.*—Botanic name: $F_1$ interspecific hybrid of *C. kousa*×*C. florida* Commercial name: Cornus×'Rutgan'.

The tree disclosed in FIG. 1 of the drawing is about 17 years old, is 6.39 meters and has a spread of 5.1 meters.

Tree: Vigorous — upright and spreading, or full — dense — somewhat vase-shaped when young, but broad and full as an older plant — hardy — very productive, i.e., very floriferous (but highly sterile).

Trunk: Medium — smooth when young, but becoming somewhat shaggy with age.

Branches: Medium — smooth.

Lenticels: Numerous — medium.

Leaves: Abundant.

*Length.*—10.3–14.0 cm (average=12.3).

*Width.*—4.8–6.6 cm (average=5.4) at widest point. Medium size. Dark green — Upper surface: RHS Chart 137A. Lower surface: RHS Chart 138B.

*Leaf shape.*—Elliptic, with acuminate tip and cuneate base.

*Margin.*—Crenate.

*Petiole.*—6–13 mm in length (average=10.3 mm.

Flower buds: The true flowers are small and numerous and are borne in flower heads. The true flowers are relatively inconspicuous. The floral display is provided by the large floral bracts that immediately subtend the flower heads. Hardy: U.S.D.A. Plant Hardiness Zone 6a (−10 degrees F.).

Bracts:

*Color.*—Upper surface: RHS 49A (Red Group). Lower surface: RHS 49D (Red Group).

*Size.*—Larger in size than those of the seed parent and equal in size to those of the pollen parent. When fully expanded the diameter of the inflorescence from tip to tip of the opposing inner bracts is about 116 mm; the diameter of the inflorescence as measured from tip to tip of the opposing outer bracts is about 105 mm. The average length of the inner bracts is approximately 56 mm. The average length of the outer bracts is approximately 50 mm. The average width of the inner bracts at their widest point is about 40 mm. The average width of the outer bracts at their widest point is about 46 mm. Bract length and width will vary from year to year, but the inner bracts will most likely be longer and narrower than the outer bracts each year.

*Shape.*—Bracts are sessile, nearly rounded to obovate with short, acute tips and tapered bases. The inner bracts are longer and narrower than the outer, or lower bracts. The margins of the basal one-third of adjacent bracts typically overlap.

*Peduncle length.*—Each flower head is borne on a peduncle, the average length being about 5 cm at the time of flowering, whereas those of the *C. kousa* parent average approximately 7 cm in length and those of the *C. florida* parent average about 3 cm at the time of flowering. Peduncle length varies from year to year but the relative difference between the three plants (two parents and hybrid) will be quite consistent.

Tree:

*Flowers.*—Date of first and full bloom: Anthesis of the tiny, relatively inconspicuous true flowers generally commences two to four days following the onset of the ornamental display of the large floral bracts. The average number of true flowers per flower head (47) is intermediate to that for the *C. kousa* parent (average=49) and that for the *C. florida* parent (average=29). Flowering period is early compared with plants of *C. kousa* and late compared with plants of *C. florida.* Period of floral display (floral bracts) is intermediate to that of plants of the parent species; i.e., occurs in mid-May, commencing one to three days after completion of the floral display (floral bracts) of most plants of *C. florida* and ending a few days prior to the onset of the floral display (floral bracts) of most plants of *C. kousa.*

*Fruit.*—Fully developed fruit have not been observed, as plants of this new $F_1$ interspecific hybrid are highly sterile. However, some flower heads may persist throughout the growing season and, occasionally, the fleshy portion of small, parthenocarpic (seedless) fruit will develop, albeit incompletely. However, there is no formation of a syncarp as in *C. kousa,* as the flowers in this new hybrid are distinct and separate in the flower head, or on the receptacle.

Resistance to:

*Insects.*—Good. In field plantings with *C. kousa* and *C. florida,* the Dogwood Borer has ravaged the plants of *C. florida,* but has not infested plants of my new $F_1$ interspecific hybrid.

*Diseases.*—Good. In field plantings with *C. florida* and *C. kousa,* my new $F_1$ interspecific hybrid has been free of the 'dogwood decline' that has decimated cultivated and wild stands of *C. florida* in recent years.

I claim:

1. A new and distinct cultivar of dogwood tree, substantially as herein shown and described, characterized particularly as to novelty by the unique combination of its vigor and highly floriferous small flowering form similar to its seed parent *C. kousa* in its upright habit but more spreading and fully branched as a young plant, producing floral bracts of a pinkish coloration, and intermediate to the two parent species in regard to characteristics of the overwintering flower buds and time of flowering, this hybrid being highly sterile, and resistant to disease and insects.

* * * * *

UNITED STATES PATENT AND TRADEMARK OFFICE

CERTIFICATE OF CORRECTION

PATENT NO. : Plant 7,207

DATED : March 27, 1990

INVENTOR(S) : Elwin R. Orton, Jr.

It is certified that error appears in the above-identified patent and that said Letters Patent is hereby corrected as shown below: On the title page, Item [54] and Column 1, In the Title, 'STELLAR PINK' should read –'RUTGAN'–.

Signed and Sealed this

Sixth Day of July, 1999

*Attest:*

Q. TODD DICKINSON

*Attesting Officer*

*Acting Commissioner of Patents and Trademarks*